US012766162B2

(12) United States Patent
Virno et al.

(10) Patent No.: US 12,766,162 B2
(45) Date of Patent: Oct. 20, 2026

(54) ORAL SOLUTION BASED ON CITICOLINE AND NICOTINAMIDE FOR USE IN THE TREATMENT OF GLAUCOMA

(71) Applicant: Omikron Italia S.r.l., Rome (IT)

(72) Inventors: Cristiano Virno, Rome (IT); Marco Malizia, Rome (IT)

(73) Assignee: Omikron Italia S.r.l., Rome (IT)

( * ) Notice: Subject to any disclaimer, the term of this patent is extended or adjusted under 35 U.S.C. 154(b) by 409 days.

(21) Appl. No.: 18/560,536

(22) PCT Filed: May 6, 2022

(86) PCT No.: PCT/IB2022/054202
§ 371 (c)(1),
(2) Date: Nov. 13, 2023

(87) PCT Pub. No.: WO2022/238833
PCT Pub. Date: Nov. 17, 2022

(65) Prior Publication Data
US 2024/0261315 A1 Aug. 8, 2024

(30) Foreign Application Priority Data
May 10, 2021 (IT) ........................ 102021000011852

(51) Int. Cl.
*A61K 31/7068* (2006.01)
*A61K 9/00* (2006.01)
*A61K 31/455* (2006.01)
*A61P 27/06* (2006.01)

(52) U.S. Cl.
CPC ........ *A61K 31/7068* (2013.01); *A61K 9/0053* (2013.01); *A61K 31/455* (2013.01); *A61P 27/06* (2018.01)

(58) Field of Classification Search
CPC ...... A61K 47/26; A61K 47/02; A61K 31/455; A61K 9/08; A61K 9/0095; A61K 47/12; A61K 31/7068; A61K 2300/00; A61P 25/28
USPC ........................................................... 514/49
See application file for complete search history.

(56) References Cited

U.S. PATENT DOCUMENTS 8,822,429 B2 * 9/2014 Virno ........................ A61P 9/12 514/52
10,576,039 B2 * 3/2020 Virno ...................... A61P 27/06

FOREIGN PATENT DOCUMENTS

CN 1079650 A 12/1993
WO WO2020/106746 A1 * 5/2020 ............. A61K 47/26
WO WO-2022238833 A1 11/2022

OTHER PUBLICATIONS

Ottobelli et al, Ophthalmologica, 2013, 229, 219-226.*
Williams et al, Science, 2017, 355, 756-760.*
Pujari et al, World Journal of Pharmaceutical Research, 2019, 8(13), 768-783.*
Bubella, M.R., et al., “Neuroprotection of patient with open-angle chronic Glaucoma: role of citicoline in oral solution,” Ottica Fisiopatologica 16:171-177, PubliComm, Italy (Sep. 2011).
International Search Report and Written Opinion for International Application No. PCT/IB2022/054202, European Patent Office, Netherlands, mailed on Jul. 15, 2022, 12 pages.
Oddone, F., et al., “Citicoline in Ophthalmological Neurodegenerative Disease: A Comprehensive Review,” Pharmaceuticals (Basel) 14(3):281, MDPI, Switzerland (Mar. 2021).
Ottobelli, L., et al., “Citicoline oral solution in glaucoma: is there a role in slowing disease progression?” Ophthalmologica 229(4):219-226, Karger, Switzerland (May 2013).
Williams, P.A., et al., “Vitamin B3 modulates mitochondrial vulnerability and prevents glaucoma in aged mice,” Science 355(6326):756-760, American Association for the Advancement of Science, United States (Feb. 2017).

* cited by examiner

*Primary Examiner* — Ganapathy Krishnan
(74) *Attorney, Agent, or Firm* — Daniel A. Blasiole; DeWitt LLP

(57) ABSTRACT

The present invention relates to a composition for oral use in the form of aqueous solution comprising citicoline and nicotinamide and said composition for use in the treatment of glaucoma. The present invention further relates to the pharmaceutical form in aqueous solution characterized by high bioavailability.

11 Claims, 5 Drawing Sheets

ORAL SOLUTION BASED ON CITICOLINE AND NICOTINAMIDE FOR USE IN THE TREATMENT OF GLAUCOMA

FIELD OF THE INVENTION

The present invention, in general, relates to a composition for oral use in form of aqueous solution comprising citicoline and nicotinamide. Said composition is utilized for use in treating neurodegenerative pathologies, in particular for use in the treatment of glaucoma.

STATE OF ART

Glaucoma is a neurodegenerative ophthalmic chronic pathology characterized by a damage to the Retinal Ganglion Cells (RGC), to the optical nerve fibres, and by a progressive reduction in the visual field. It is the second cause of irreversible blindness and the most frequent, and even the most insidious, form is the Open Angle Glaucoma (OAG). Age, familiarity, severe myopia, high IntraOcular Pressure (IOP) are only some of the risk factors which can increase the probability of developing the disease. High IOP represents the only modifiable risk factor and upon this the first therapeutic approach is based, through hypothesizing eye drops or, in case should it be not enough, laser or surgery.

Histological and in-vivo imaging studies in man have demonstrated that, in presence of glaucoma, the whole optical route is involved in a transsynaptic degeneration process which creates damages to the optic nerve and brain structures, such as geniculate nucleus and visual cortex, seat of the primary visual area. Such process, activated by the hyperbaric damage, causes as anatomical and functional consequence the progressive thinning of the layer of the retinal nerve fibers, the progressive excavation of the optic nerve head and, then, the compromise of the visual function, characterized by the onset and by the progressive extension of scotomatous areas (of not vision) in the visual field.

Recent studies have demonstrated that glaucoma is a neurodegenerative pathology like Alzheimer and Parkinson. They are diseases in which neurons localized in different seats are involved by degeneration and die due to apoptosis. In Alzheimer disease the process starts in the hippocampus, in Parkinson disease in substantia nigra and in glaucoma the process starts at the level of the retinal ganglion cells.

Following the primary insult, having hyperbaric nature, the neurone apoptosis is triggered, which interferes with the usual blood supply at the level of the capillary district of this structure, and the regular axonal, both antegrade and retrograde, transport of metabolites and neurotrophins, essential for survival of ganglion cell, is compromised. Apoptosis is responsible for the secondary insult, linked to the mechanisms of local excitotoxicity due to the hyperstimulation of the NMDA receptors by the glutamate freed by the cells in apoptosis. Glutamate, in fact, if present in excessive concentration in the extracellular space hyperstimulates the NMDA receptors on the surface of the surrounding neurons, which determine the opening of channels for $Ca^{2+}$, trigger of the biochemical cascade leading to the apoptosis of the neurone itself; then, a mechanism, capable of self-feeding even in absence of the primary insults, is established.

It was demonstrated that glaucoma damages the neurons through different mechanisms thereamong oxidative stress, neuroinflammation and mitochondrial dysfunction. Oxidative stress, linked to the accumulation of free radicals in presence of high IOP, hits the particularly sensitive cells, as CGR are, by putting at risk the functionality of mitochondria, which are intracellular organelles providing energy and guaranteeing different functions (for example, cell homeostasis regulation). The retinal ganglion cells have more mitochondria than any neurone of the central nervous system since, for their correct operation, require a very high and continuous energy intake. When the oxidative stress damages the mitochondria, they do not succeed in providing the amount of energy required to the retinal ganglion cells which undergo dysfunction and, in the most serious cases, apoptosis.

The functional result of this degeneration involving the optical pathways is a gradual narrowing of the visual field, with areas of not vision (scotomatous areas) which generally appear at first in the peripheral portion and then extend up to the central areas, until the complete loss of vision.

Several clinic evidence have confirmed by now that the glaucomatous patients, notwithstanding an effective pressure control, continue over the years to undergo a damage progression with consequent reduction in the visual field. The EMGT (Early Manifest Glaucoma Trial) Study implemented by the National Institute of Health highlighted that notwithstanding the hypotensive control, 45% of the glaucomatous patients has a progressive campimetric damage.

Several studies evaluated the possibility to reduce or at least to slow down such degenerative process, through the intake, in addition to the hypotensive drugs, of molecules called neuroprotective molecules directly aiming at maintaining functionality and reducing vulnerability of CGR.

A particular interest in the field of the neuroprotection is addressed to citicoline (citidin-5'-difosfocholine) and to nicotinamide (or vitamin B3), for their action mechanism and for the experimental and clinical results obtained on glaucomatous patients.

The neuroprotective proprieties of citicoline in the glaucomatous pathology were evaluated for the first time with the injective formulation, already used for some time in the neurodegenerative pathologies of the central nervous system. Vimo et al. in fact demonstrated, with a study with a 10-year follow-up, the reduction of the perimetric defect, evaluated as areas of not perception, obtained through treatment with citicoline intramuscularly in glaucomatous patients. These results were confirmed by an additional long-term study (8 years of follow-up), which confirmed the effectiveness of citicoline through a significant improvement of the retinal and cortical bioelectric responses in patients with OAG.

The administration of citicoline intramuscularly for treating glaucoma then resulted to be effective on glaucomatous patients even if clearly very uncomfortable for a chronic patient and for the need for having available a person capable of performing the injections.

The results obtained with the systemic form encouraged the development of a citicoline-based oral formulation, so that it increased the compliance to the treatment of the glaucomatous patients. The study on patients with controlled IOP (<18 mmHg), in treatment with b-blockers, showed that the treatment with oral citicoline induced an improvement in the width of PERG signal ($p<0.01$) and a decrease in latency time of VEP ($p<0.01$) compared to the checks towards the basal values. Based upon these results a formulation in oral solution was then developed whereon the following clinical study (1) was performed, implemented at the University in Palermo, which demonstrated, in double blind versus placebo, that citicoline in oral solution (500 mg/die) slows down the loss of nervous fibres at the retinal layer through GDX with respect to the patients treated with antihypertensive therapy only. It was further demonstrated that cycles of citicoline in oral solution allow to slow down the loss of electro-physiologically demonstrated visual functionality (latency time at pEV and width at pERG). Citicoline in oral solution in fact improved the electro-functional parameters, by increasing, in particular by 100%, the width of P50-N95 tract of pERG.

As far as nicotinamide is concerned, a very recent experimental study carried out at Jackson Laboratory/Howard Hughes Medical Institute and Bascom Palmer Eye Institute di Miami, and whose results were published by the magazine Science, demonstrated that vitamin B3 reduces the incidence of glaucoma in the treated group (2). The researchers performed a series of genetic, metabolic and neurobiological tests on a group of mice which are genetically modified to be predisposed to develop glaucoma, as well as on a healthy control group. The results confirmed that nicotinamide decreases with age and the administration of this molecule, in addition to drinking water, protected the mice from onset of glaucoma.

In the light of what said, the problem of providing new compositions for treating glaucoma is still very much felt.

SUMMARY OF THE INVENTION

The technical problem placed and solved by the present invention is to provide a composition for oral use for the treatment of glaucoma, characterized by a high bioavailability, in particular comparable to that of a solution administered intravenously.

Such problem is solved by a composition for oral use, in the form of aqueous solution, based on citicoline and nicotinamide. Glaucoma, in fact, has a multifactorial pathogenetic nature and it is characterized by a transsynaptic degeneration running along the optical pathways, from the retinal ganglion cells to the visual cortex and which causes the gradual loss of visual field.

Advantageously, the authors of the present invention found that the herein described formulation in aqueous solution determines a so high bioavailability of citicoline and nicotinamide that it could be compared to the one obtained when these active principles are administered intravenously. When the active principle is in solution, in fact, it is in a form immediately available to the absorption step and this guarantees a greater bioavailability with respect to when it is administered at the solid state, for example in a tablet or in a suspension.

The subject composition, with respect to the formulations of prior art, then has the enormous advantage of joining a high bioavailability of these two active principles, comparable to the intravenous one, to the classical advantages of the oral route, such as high compliance, low costs and safety. As highlighted by the results of the clinical studies shown in the experimental section of the present application, the administration of a composition for oral use, in the form of aqueous solution, as herein described in patients affected by glaucoma, revealed to be surprisingly more effective in particular in terms of improvement of the visual function, of structural protection of the retinal layers with respect to what predictable based upon the sum of the effect of citicoline and nicotinamide administered individually, by confirming an action synergism between the two active principles in the composition of the invention.

Therefore, the present invention relates to a composition for oral use in form of aqueous solution comprising citicoline and nicotinamide and the use thereof in the treatment of glaucoma.

The present invention also relates to the method for preparing said composition.

Preferred features of the present invention are set forth in the depending claims.

Other advantages, features and use modes of the subject invention, will result evident from the following detailed description of some embodiments, shown by way of example and not for limitative purposes.

BRIEF DESCRIPTION OF FIGURES

The present invention and the following detailed description of the preferred embodiments can be better comprised with reference to the following figures.

DETAILED DESCRIPTION OF THE INVENTION

Figure 1A:
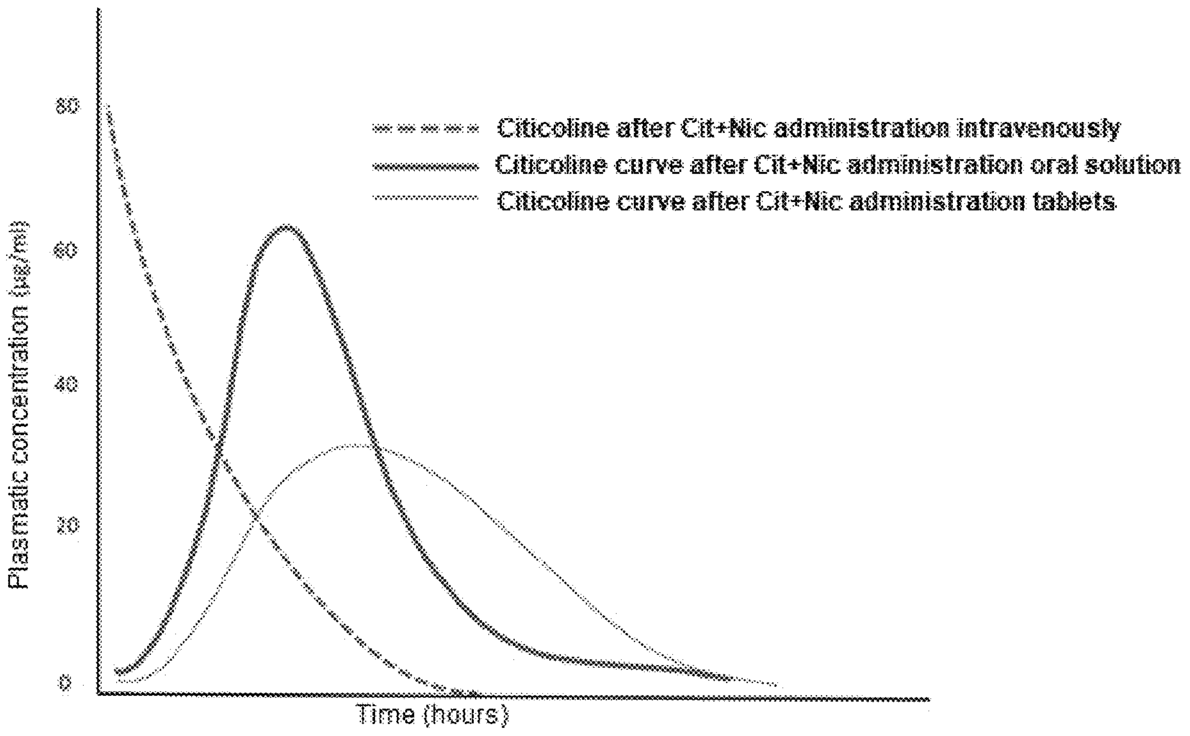
FIG. 1. Curves of bioavailability of citicoline (1a) and nicotinamide (1b) administered intravenously, in oral solution and in tablets. The bioavailability of citicoline and of nicotinamide in oral solution are near to 100%.

The present invention relates to a composition for oral use in form of aqueous solution comprising citicoline and nicotinamide.

Citicoline, the structure thereof is the following

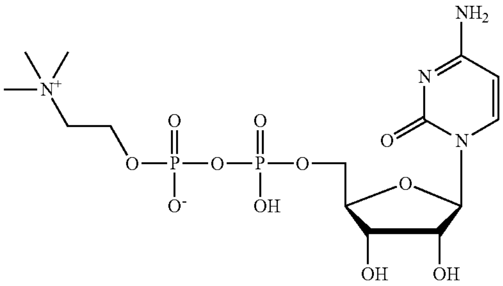

is a nootropic agent with an effectiveness widely recognized in pathologies of the central nervous system, such as Parkinson's disease, multiple sclerosis, trauma and brain injuries, cerebrovascular events, cognitive disorders.

Citicoline acts at different levels with a multifactorial action mechanism: it preserves the levels of cardiolipin and sphingomyelin, phospholipidic components respectively of the internal mitochondrial membrane and of the membrane of the axons of the retinal ganglion cells, it restores phosphatidylcholine, one among the most abundant phospholipids in the nerve cell membranes, it preserves the mitochondrial function, by preventing the oxidative damage and the onset of neuronal apoptosis, it stimulates glutathione synthesis, it prevents glutamate excitotoxicity, by reducing the concentrations thereof, it stimulates the myeline synthesis, it leads to the improvement of the integrity of neuronal membrane, it increments the synthesis of neurotransmitters, such as acetylcholine and dopamine, it prevents the endothelial dysfunction. In particular, its effect on the phospholipids is the basis of its structural action, which is accompanied by an additional functional action on the neurotransmitters.

Recent evidence has demonstrated that citicoline is capable of interacting with proteasome, molecular complex responsible for proteolysis at cellular level. Dysfunctions affecting proteasome translate into the accumulation of proteins according to a typical picture of the neurodegenerative pathologies. Citicoline stimulates significantly the enzymatic properties of the complex against proteins, thereamong the amyloidogenic ones (α-synuclein), thus exerting a neuroprotective effect. Citicoline, taken in oral solution or parenterally, is immediately broken down in P-choline and cytidine-5-monophosphate (CMP). The phosphorylated compounds do not cross the blood-brain barrier, then P-choline and CMP are further dephosphorylated to choline and cytidine. Choline crosses the blood-brain barrier and in SNC it is phosphorylated to P-choline, whereas cytidine in man is converted into uridine, which in turn crosses the blood-brain barrier, in SNC it is phosphorylated to uidine triphosphate (UTP) and converted into CTP. P-choline and CTP form again citicoline thanks to the action of cytidine-5'-triphosphate phosphocholinecytidil-transferase enzyme, with reversible reaction, the direction and speed thereof depend upon the concentration of the substrates; a fundamental importance derives therefrom, higher than other compounds of bioavailability of the taken preparation.

As far as the elimination is concerned, a low faecal elimination was observed, index of optimum absorption and an elimination by respiratory ($CO_2$) and urinary route. The elimination of the marked products, in five days, was only by 16%, by demonstrating that the catabolites were incorporated in the biological structures. The elimination is biphasic, the first phase takes place in few hours and the second one very slowly. This course is a further proof that the absorbed citicoline incorporates in the cellular membranes and it is then eliminated by following the physiological metabolic fate of the biological structures.

Nicotinamide, or vitamin B3, whose structure is represented in the following image:

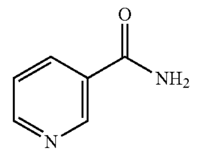

belongs to the group of water-soluble vitamins, which have to be regularly taken through food. It is the precursor of NAD and NADP oxide-reductive coenzymes, which play a key role in the oxidation/cellular reduction reactions and are associated to catabolic and anabolic processes. Thanks to the above-mentioned action mechanism, nicotinamide explicates different actions and, in particular, has a fundamental role in the operation of the nervous system, by favouring synaptic plasticity and axonal growth.

Nicotinamide deficiency and consequently NAD and NADP reduction, like advancing age, are factors predisposing for the development of glaucoma since the make the optic nerve and the nervous cells more vulnerable to the effects of the increase in the intraocular pressure.

The intestinal absorption of nicotinamide taken orally is high and can reach even 70%. This mostly takes place by diffusion mediated by sodium-depending carrier. Nicotinamide is the main form of vitamin B3 existing in the bloodstream. From the blood, it moves through the cellular membranes by simple diffusion, however, the transport in the kidney tubules and in the erythrocytes requires a carrier. Inside the cell, nicotinamide is used to synthetize NAD, which then can be phosphorylated to NADP; both of them can accept two electrons and one proton, forming NADH and NADPH. Nicotinamide is converted into NAD by reaction with 5-phosphoribosyl-1-pirophosphate and ATP and NAD is converted into NADP by reaction with ATP. The main route of catabolism of nicotinamide is methylation in the liver and subsequent oxidation. Nicotinamide is metabolized to N-methyl-nicotinamide (NMN), with the participation of ATP and $Mg^{2+}$ and S-adenosylmethionine as methyl donor. NMN can be oxidized to N-methyl-2-pyridone-carboxamide (2-Pyr) and N-methyl-4-pyridone-carboxamide (4-Pyr), both of which are both in plasma and urine.

According to an embodiment of the present invention, citicoline is present in the composition in a concentration comprised between 25 mg/ml and 100 mg/ml, preferably in the range between 49.75 and 50.25 mg/ml, or approximately 50 mg/mL, and nicotinamide has a concentration comprised between 5 mg/ml and 20 mg/ml, preferably in the range between 9.95 and 10.05 mg/ml, or approximately 10 mg/mL.

According to an additional embodiment, the composition has a ratio between citicoline free acid and nicotinamide preferably comprised between 2.5:0.5 and 10:2.

According to a preferred embodiment, the composition has a ratio between citicoline free acid and nicotinamide equal to 5:1.

Another embodiment of the present invention, according to the herein-described other embodiments, can include potassium sorbate, in a concentration comprised between 1.34 mg/ml and 3 mg/ml, preferably in the range between 2.67 mg/ml and 2.69 mg/ml, or approximately 2.68 mg/mL.

The potassium sorbate, the formula thereof is represented below,

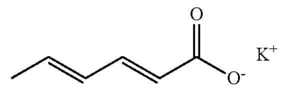

is used as preservative, above all in cosmetic and food field, thanks to its antifungal and antibacterial properties. It is active only at acid pH and it is very soluble in water. It is synthetized by making to react the ascorbic acid, present in nature, with potassium hydroxide (KOH).

According to an embodiment of the subject invention, the composition can include even 60% sodium lactate, in a concentration comprised between 2.5 mg/ml and 7 mg/ml, preferably in the range between 4.975 and 5.025 mg/ml, or approximately 5 mg/nL.

The sodium lactate, the formula thereof is represented in the below image,

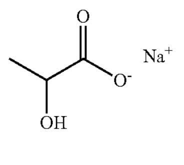

is the sodium salt of the lactic acid, of natural origin, with antioxidant function. It also acts as acidity regulator, humectant, anti-charging agent, emulsifier and/or thickener. It is a water-soluble compound, not particularly sensitive to high temperatures.

According to another embodiment of this invention, the composition can further include fructose, in a concentration comprised between 150 mg/ml and 400 mg/ml, preferably in the range between 298.5 and 301.5 mg/ml, or approximately 300 mg/mL.

The fructose, which has as structure formula the following one,

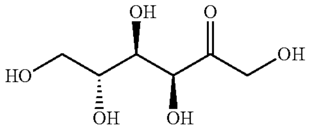 [SMILES: O=C(CO)[C@@H](O)[C@H](O)[C@H](O)CO]

is a monosaccharide, topological tisomer of glucose, therefrom it differentiates since it is ketose instead of aldose. It is important in human and animal nutrition and often it is used as sweetener, since, with respect to sucrose, has a greater sweetening power, it has a slightly lower caloric intake and it has a lower glycemic index.

An additional embodiment of the present invention can include even anhydrous acid, in a concentration comprised between 0.92 mg/ml and 2.00 mg/ml, preferably in the range between 1.82 and 1.84 mg/ml, or approximately 1.83 mg/mL.

The citric acid, represented in the following image,

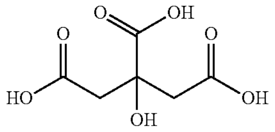

is used as aroma and preservative, in food and beverages. Moreover, it is exploited as acidulant, as emulsifier, as substitute of the lemon juice and to correct the pH of dyes; in combination with the sodium bicarbonate, it is used even for effervescent preparations.

A preferred embodiment provides that the composition, according to any one of the described embodiments, comprises, or is replaced by, citicoline, in a concentration equal to 50 mg/mL, nicotinamide, in a concentration equal to 10 mg/mL, potassium sorbate, in a concentration equal to 2.68 mg/mL, 60% sodium lactate, in a concentration equal to 5 mg/mL, fructose, in a concentration equal to 300 mg/mL, and citric acid, in a concentration equal to 1.83 mg/mL.

According to an embodiment of the subject invention, the composition, according to the other herein described embodiments, can further include one or more excipients and/or additives. Characteristic examples of excipients for compositions for oral use in liquid form are sorbitol, glycerol, sucrose, glycerine, sodium phosphate, methyl p-oxybenzoate, propyl p-oxybenzoate, water-soluble aroma, etc.

An embodiment of the present invention provides that said composition, according to any one of the herein described embodiment, has a high bioavailability of citicoline, in particular that its bioavailability is comprised between 90% and 100%, preferably it will be at least 95%, preferably at least 98%.

Under the term "bioavailability", one refers to the amount of active principle, in this case of citicoline, in the bloodstream, which define its biological availability. It is assumed that there is correspondence between the tissue concentration and the plasmatic one since an equilibrium is established between the central compartment and the peripheral tissues. The bioavailability profile is described by the curve of plasmatic concentration versus time and the pharmacokinetic parameters which are used to describe it are the maximum plasmatic concentration ($C_{max}$), which is directly proportional to the absorption speed, the time to reach the maximum plasmatic concentration ($t_{max}$), which is inversely proportional to the absorption speed, and the area under the curve (AUC), which is directly proportional to the amount of absorbed active principle. The bioavailability can be meant both as absolute and relative.

In particular, under the expression "absolute bioavailability" the ratio between the area under the curve of an extravascular route, in this case the oral route, and the area under the curve of the intravenous route is meant, each one corrected depending upon the administered dose. This parameter allows to understand how much less citicoline and nicotinamide is absorbed when administered orally, considering that the 100% bioavailability is reached only intravenously, wherein the absorption step is missing.

On the contrary, under the expression "relative bioavailability" one refers to the ratio between the areas under the curve generated by a same active principle which was administered by two different routes, different from the intravenous one, or administered through a same route but formulated differently (for example active principle formulated as tablet and as oral solution).

Unless differently designated in the present description, the percentage of bioavailability is absolute bioavailability.

According to a preferred embodiment the composition is formulated as aqueous solution.

The compositions for oral use can be very different therebetween in terms of bioavailability, speed and absorption profile and, the active principle being equal, the formulation is a determining factor. The formulations by oral route can be solid (tablets, capsules, late formulations, gastroprotective formulations, etc.) or liquid (suspensions and solutions). Whatever formulation is used, a drug administered by oral route, in order to be absorbed, has necessarily to dissolve in the gastrointestinal liquids. The oral solid formulations, then, have to release the active principle. This is a two-step process which comprises the breaking-down of the solid formulation and the solubilization of the drug itself. Different solid forms of a same active principle can have different absorption profiles, depending upon breaking-down and solubilization time, which can be significantly different depending upon the used excipients, the external factors or the chemical-physical properties.

The liquid formulations (syrups, phials, sachets to be dissolved etc.) can be suspensions or solutions, and indeed the latter are capable of guaranteeing a greater bioavailability. The formulations in suspension, in fact, have the active principle under the form of minute solid particles, suspended in the liquid phase, then, even if they have no breaking-down step, the particles should go into solution to be absorbed. The solutions, instead, advantageously have the already dissolved active principle, then in a form immediately available to the absorption step, and this guarantees a greater bioavailability.

According to an additional embodiment of the of the present invention, based upon any one of the herein described embodiments, the aqueous solution has a pH comprised between 3.9 and 4.1, preferably 4.00.

According to an additional embodiment of the present invention, based upon any one of the herein described embodiments, the aqueous solution has a density comprised between 1.116 and 1.156 g/ml, preferably 1.136 g/ml.

According to an embodiment of the present invention, the composition is for use in the treatment of a neurodegenerative pathology.

Under the expression "neurodegenerative diseases" a series of conditions is meant affecting above all the neurons of the central nervous system is meant. They are debilitating and non-curable pathologies causing the progressive degeneration and/or death of nerve cells.

According to a preferred embodiment of the subject invention, the composition is for use in the treatment of glaucoma. The scientific literature has demonstrated that citicoline has a neuroprotective effect, since it slows down the progression of the campimetric damage in glaucomatous patients, and that nicotinamide increases the functionality of the internal retinal layer and improves the visual field. The composition, the present invention relates to, then gives the possibility of providing neuroprotection on two fronts, since the action of nicotinamide combines to the neuroprotective effect of citicoline in a specific formulation having high bioavailability.

According to an embodiment of the subject invention, the composition is administered in a volume between 5 ml and 20 ml, or approximately 10 ml once a day, preferably in the morning, in the above-mentioned dosages.

The present invention further relates to the method for preparing the composition, as described in any one of the embodiments thereof. In particular, such method provides the dissolution in water and the mixing of the elements constituting the composition.

EXAMPLES

Example 1. Preparation of a Composition According to the Invention and Bioavailability Study Aqueous solution comprising: potassium sorbate (2.6 mg/mL), 60% lactate solution (5 mg/mL), fructose (300 mg/mL), citicoline free acid (50 mg/mL), nicotinamide (10 mg/mL), anhydrous citric acid (1.83 mg/mL).

Figure 2:
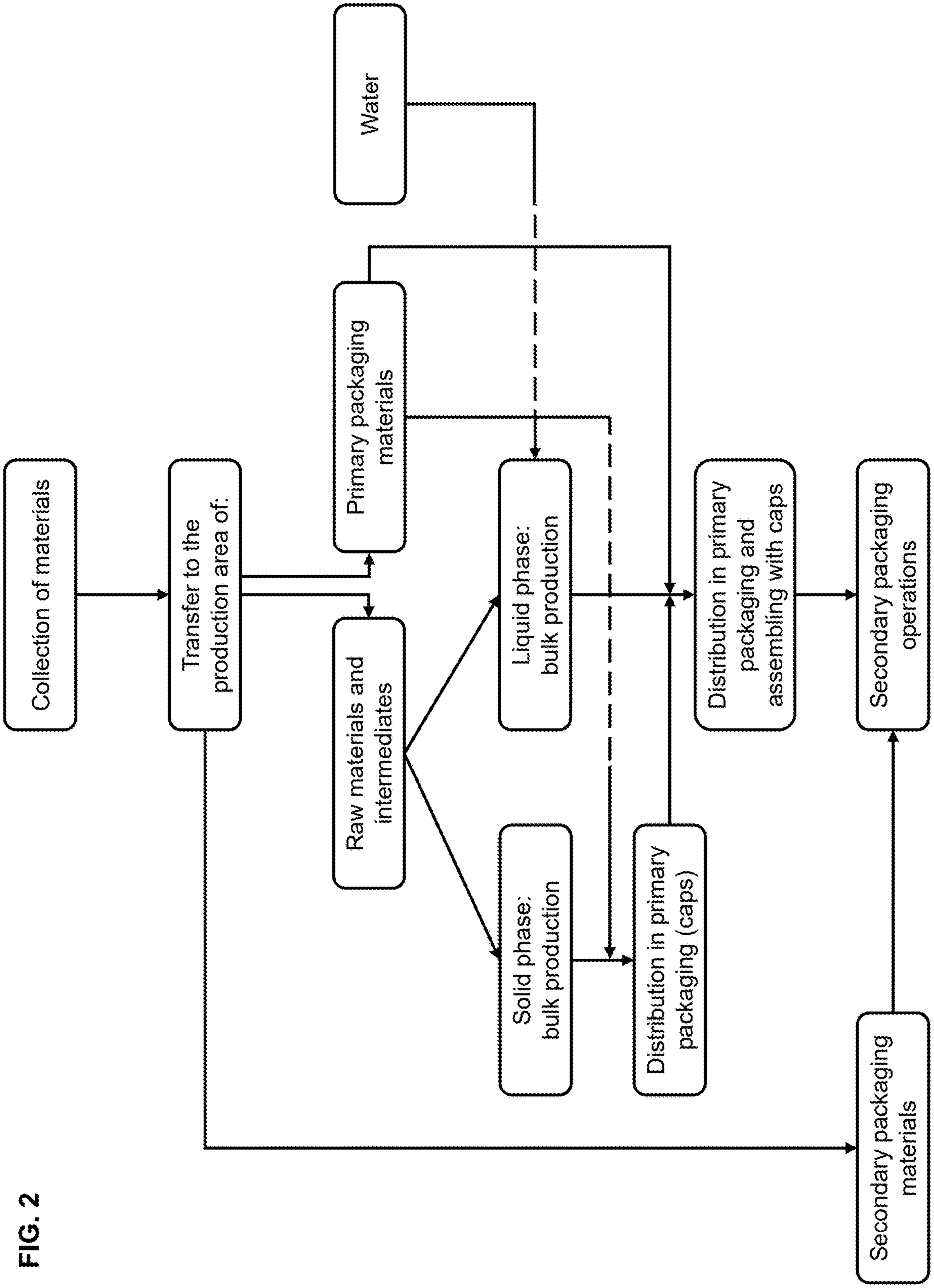
FIG. 2. Flow diagram of the method for the production of the aqueous solution according to a preferred embodiment.

- Aspect: limpid solution
- Colour: colourless
- pH: 4.00
- Density: 1.136 g/ml
- Preparation method: the aqueous solution was prepared with citicoline free acid, nicotinamide and the excipients usually used for this type of formulations, such as: potassium sorbate as preservative, sodium lactate and citric acid as acidity regulators, fructose as sweetener. The components were weighed and mixed, according to the above-mentioned amounts, for the relative dissolution in water. Solution pH and density were regulated until the above-defined values. The composition was prepared according to the flow diagram shown in FIG. 2.

Methods

Bioavailability Study

The bioavailability of citicoline existing in the composition, the invention relates to, was surveyed by making a bioavailability study on Sprague-Dawley rats. In particular, 30 Sprague-Dawley male rats, weighing 175 and 225 g, were subjected fasting 16 hours before administration. The animals were divided into three groups:

- Group 1: 10 rats treated with Citicoline+Nicotinamide intravenously
- Group 2: 10 rats treated with Citicoline+Nicotinamide in oral solution
- Group 3: 10 rats treated with Citicoline+Nicotinamide in tablets For the preparation of the radiomarked formulations 14C-methylCiticoline and 714C-Nicotinamide were used.

The preparations were purified by ion-exchange chromatography by using isobutyric acid:water-ammonia:EDTA (500:280:21:8), n-butanol:acetic acid:water (12:3:5), ethanol:1 mol/l ammonium acetate pH 7 (5:2), ethanol:saturated borax (8%):0.5 mol/l EDTA:5 mol/l ammonium acetate (220:80:0.5:20).

The samples were analysed with a liquid scintillator counter LSC, according to the programme for $^{14}C$.

For the quantitative analysis Packard soluene (solubilizing agent), $H_2O_2$ (bleaching agent) and Packard Instagel (scintillator) were used as reagents.

The formulations were administered at the dose of 5 mg/kg respectively: Group 1, intravenously in the jugular vein; Group 2, in oral solution administered by nasogastric tube; Group 3, in tablets dissolved in saline solution and administered by nasogastric tube.

The collections of blood samples of about 100 ml were obtained at programmed time (after administration at 10', 20', 30', 1 h, 2 h, 3 h, 4 h, 5 h, 6 h, 7 h, 24 h).

Figure 1B:
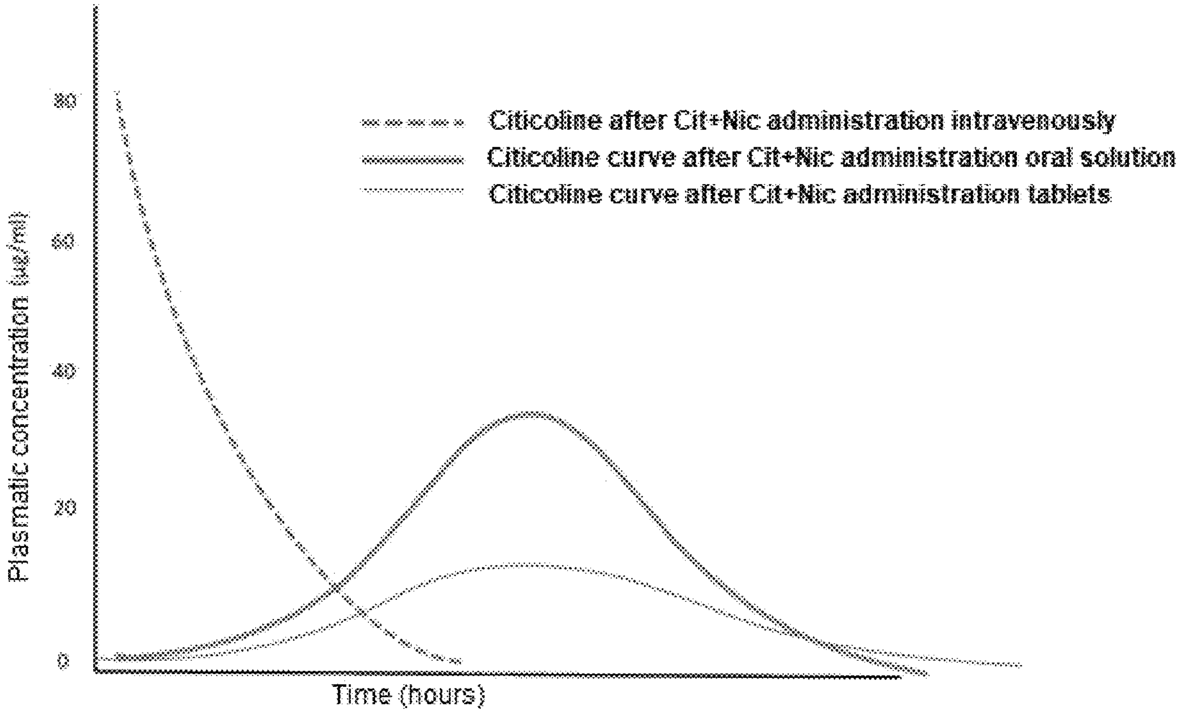

The calculation of absolute bioavailability was performed by means of the ratio of the area under the curve (AUC) of the average values obtained respectively for the intravenously/aqueous solution and intravenously/tablet administrations (FIG. 1).

Among the pharmaceutical forms administered orally, the formulation in aqueous solution based on citicoline+nicotinamide showed a greater bioavailability of its active principles with respect to the tablet. The bioavailability of Citicoline+Nicotinamide administered in aqueous solution resulted to be comparable to that of the intravenously administration.

Bioavailability of $^{14}$Citicoline after administration of aqueous solution based in Citicoline+Nicotinamide:

$$\frac{AUC_{0-24}\text{ aqueous solution}}{AUC_{0-24}\text{ intravenously}} = 0.92$$

$AUC_{0-24}$ intravenously: 77.42; $AUC_{0-24}$ aqueous solution.: 71.58 Bioavailability of $^{14}$Nicotinamide after administration of aqueous solution based on Citicoline+Nicotinamide:

$$\frac{AUC_{0-24}\text{ aqueous solution}}{AUC_{0-24}\text{ intravenously}} = 0.91$$

$AUC_{0-24}$ intravenously: 70.55; $AUC_{0-24}$ aqueous solution.: 64.20

The obtained results demonstrated a bioavailability of citicoline and nicotinamide, formulated as composition for oral use in aqueous solution, close to 100%. Such result is to be attributed to the pharmaceutical form, since the oral solution makes the active principles immediately available for the absorption and guarantees a bioavailability comparable to the injective route (FIG. 1).

Example 2. In Vivo Studies on Experimental Model of Neurodegeneration on Animal

Methods

The neuroprotective effect of Citicoline+Nicotinamide association in oral solution was evaluated in an experimental study performed on db/db mice. The db/db mice have a mutation in the leptin receptor gene and they are an animal model of retinal neurodegeneration. Such model is useful to mime the pathophysiological events which are found in neurodegenerative pathologies such as glaucoma.

20 db/db rats (BKS.Cg-+Leprdb/+Leprdb/OlaHsd, males, 10 weeks) were randomized in 5 groups and treated for 15 days by oral route with oral solutions based on:

1. Citicoline 0.5% (Cit.) in 10% lactose solution administered with nasogastric tube (SNG);
2. Nicotinamide 0.1% (Nic.) in 10% lactose solution administered with SNG;
3. Citicoline 0.5%+Nicotinamide 0.1% (Cit+Nic) in 10% lactose solution administered with SNG;
4. 10% lactose solution (Placebo) administered with SNG;
5. Healthy, non-diabetic control (Control).

On day 15, 1 hour after the administration of the several treatments, the mice were subjected to (i) very high-resolution Spectral Domain Optical Coherence Tomography (SD-OCT), to obtain, in vivo, detailed images relating to the morphology of the different retinal layers. The mice were subjected to anaesthesia induced by single intraperitoneal injection of 80 mg/ml Ketamine, xylazine 12 mg/ml (Sigma-Adrich). Subsequently, to induce mydriasis, one single drop of 0.5% tropicamide was instilled and then each mouse positioned in front of the objective of OCT.

For all animals only the right eye was examined and the average obtained from three consecutive retinal scanning for each eye was considered for each layer. The OCT images were acquired through bidimensional scanning (B-scan) combined to noise reduction software with ART (automatic real time) and with a visual field of 30 degrees focalized on the head of the optic nerve. After OCT examination the animals were sacrificed by cervical dislocation and the eyes immediately enucleated.

Through (ii) full field Electroretinogram (ffERG) the electrical activity and then the functionality of the retinal cells were evaluated. The recordings were measured by using ERG platform of Ganzfeld (Phoenix Research Laboratories, Pleasanton, CA, USA) and according to the recommendations of ISCEV (International Society for Clinical Electrophysiology of Vision).

Through immunohistochemical assays, neurodegeneration histological markers were researched (glial activation and apoptosis):

(iii) The glial activation was evaluated by means of confocal laser scanning microscopy by using antibodies directed to the glial fibrillary acidic protein GFAP (anti-GFAP of rabbit). To evaluate the level of glial activation a scoring system (from 1 to 5) was used based upon the extension of GFAP (glial fibrillary acidic protein) colouring.

The sections were fixed in methanol (−20° C.) for 2 minutes, followed by three washing with saline phosphate buffer PBS (5 minutes each one). The sections were treated with Tris Saline Buffer TBS-Triton X-100 (0.025%) and incubated in a 1% solution of bovine albumin serum BSA and 10% goat serum in PBS for 2 hours at room temperature. The sections were then incubated with anti-GFAP of rabbit overnight at 4° C. in humid atmosphere. After three washing in PBS, 5 minutes each one, the sections were incubated with the secondary antibody Alexa AF488 goat-anti-rabbit (dilution 1:200 prepared in blocking solution). The sections were washed in PBS, coloured with Hoestch and assembled with means Flourescence Mounting Medium with a cover glass. Once the mounting support has dried up, comparative digital images of the samples were recorded with a confocal laser scanning microscope Fluoview FV 1000 Olympus (Olympus, Shinjuku, Tokyo, Japan) by using identical brightness and contrast settings.

(iv) The search for events of cellular apoptosis was performed through TUNEL assay by using the kit DeadEnd™ Fluorometric TUNEL System (PROMEGA, Madison, WI, USA). The TUNEL (Terminal Transferase dUTP Nick-End Labeling) colouring was performed by using the Kit system TUNEL Fluorometric DeadEnd (PROMEGA, Madison, WI, USA). Cryosections of retina were permeabilized by incubation for 2 minutes on ice with 0.1% Triton X-100 in 0.1% sodium citrate. The secondary antibody was Alexa 488 goat-anti-rabbit. For the evaluation by means of confocal laser scanning microscopy the excitation wavelength was 488 nm (detection in the range 515-565 nm (green)).

(v) The quantification of caspase-3 and of synaptophysin was performed by means of immunofluorescence. The sections were fixed in methanol (20° C.) for 1 min and washed with buffered saline solution (PBS) 0.01 M at pH 7.4. Then, the sections were incubated in 10% solution NGS, 0.1% Triton X-100, PBS for 1 hour at room environment and subsequently incubated with a specific primary antibody (respectively anti-caspase-3 and anti-synaptophysin monoclonal antibody of rabbit) one night at 4° C. The following day, after washing, the sections were incubated with fluorescent secondary antibody Alexa 594 (anti-rabbit—Life Technologies S.A, Madrid, Spain) for 1 hour and subsequently washed. At last, the nuclei were coloured with Hoechst and assembled with Flourescence Mounting Medium (Prolunga, Invitrogen) with a cover glass. The images were acquired with a confocal laser scanning microscope (FV1000; Olympus, Hamburg, Germany). Five fields (three corresponding to the central retina and two to the peripheral one) were analysed. The fluorescence intensity of images was quantified with software ImageJ.

The statistical analysis was performed with test t of Student for independent data and ANOVA test.

A value $p<0.05$ was considered statistically significant.

Results (i) Evaluation Retinal Thicknesses OCT: the results obtained from the measurement at SD-OCT (shown in Table 1) highlighted a significant alteration in the thickness of RNFL (Retinal Nerve Fiber Layer), GC/IPL (Ganglion Cells/Inner Plexiform Layer) and INL (Inner Nuclear Layer) layers in the Placebo group (not treated db/db mice) with respect to the Healthy Control. In the diabetic mice treated with citicoline only and in the group treated with nicotinamide only we are witnessing a less reduction in the thickness of the layers with a significant difference with respect to the placebo group for the RNFL and GC/IPL layers ($p<0.05$). Surprisingly such alteration results to be annulled in the group treated with citicoline+nicotinamide, wherein no difference in the thickness of the above-mentioned layers with respect to the healthy control is highlighted, thus suggesting a synergic protective effect of the combination on the Retinal Ganglion Cells (axons and soma) against the toxic effect of the prolonged diabetes ($p<0.01$).

TABLE 1

Effect of the several treatments on the variations in the thicknesses of the various retinal layers.

| Layer (μm) | Control | Placebo | Citicoline | Nicotinamide | Citicoline + Nicotinamide |
|---|---|---|---|---|---|
| RNFL | 24.2 ± 2.4 | 19.3 ± 2.2 | 22.3 ± 1.3 $p < 0.05$ vs placebo | 21.8 ± 2.4 $p < 0.05$ vs placebo | 24.9 ± 2.1 NS vs control |
| GC/IPL | 64.7 ± 3.2 | 54.1 ± 5.0 | 59.3 ± 4.8 $p < 0.05$ vs placebo | 58.8 ± 5.2 $p < 0.05$ vs placebo | 63.3 ± 2.4 NS vs control |
| INL | 19.7 ± 2.8 | 22.0 ± 1.9 | 20.9 ± 2.5 | 21.1 ± 2.1 | 20.1 ± 2.0 NS vs control |

Figure 3:
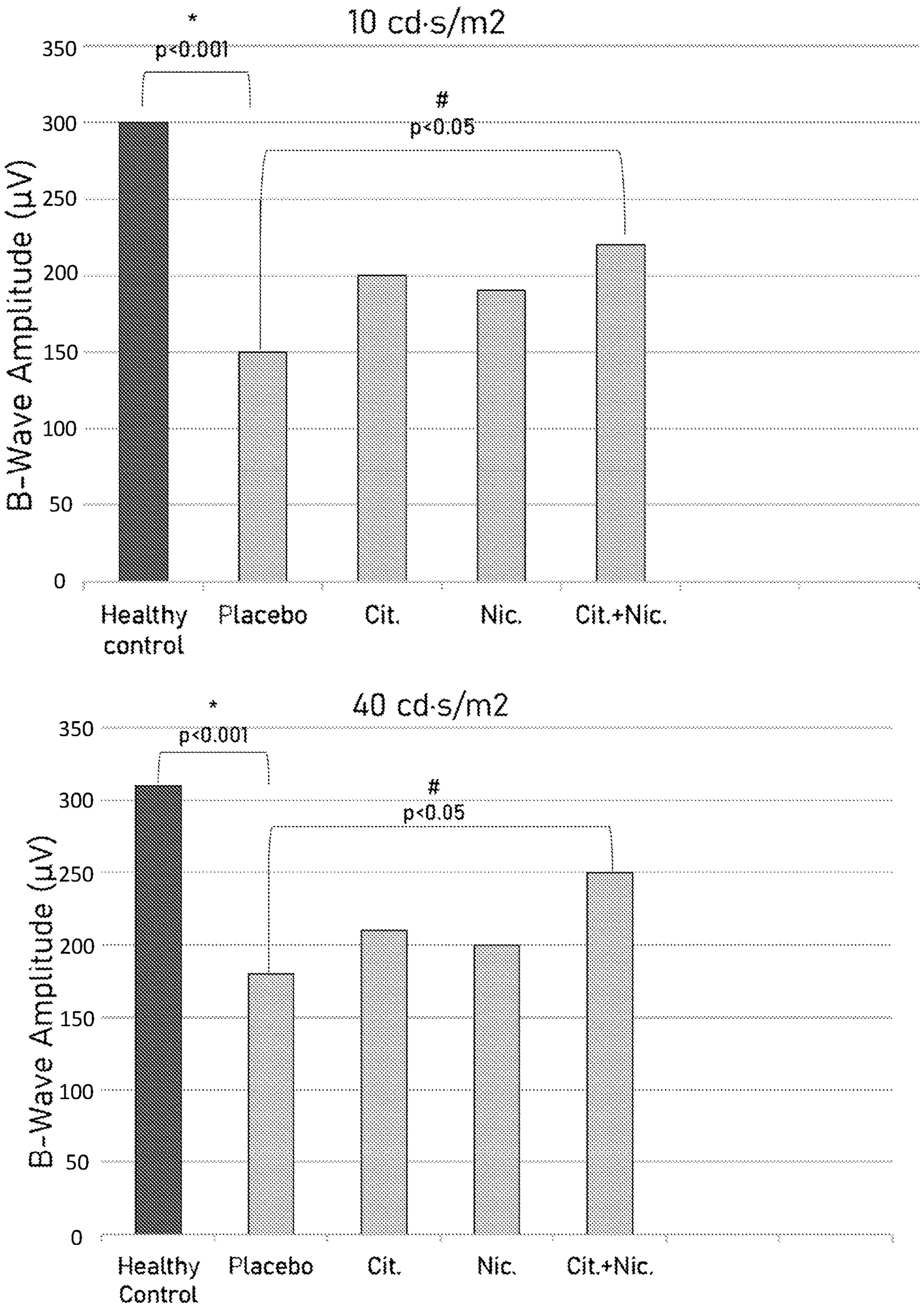
FIG. 3. Quantitative analysis of the effect of the several treatments described in the Example 2 on the electro-retinography anomalies evaluated at ERG.

(ii) Evaluation Electroretinogram: In FIG. 3 quantitative analysis of the width of wave b depending upon the flash intensity in the various groups. In db/db mice we are witnessing a reduction in the width of wave b at ERG in response to stimuli both of low intensity (10 cd s/m2) and average intensity (40 cd s/m2). Such reduction results to be attenuated with respect to Placebo both in Cit. group and in Nic group. Such effect results to be synergically strengthened in Cit+Nic group with a statistically significant difference with respect to Placebo group ($p<0.05$).

(iii-v) Immunohistochemical assays:

(iii) In the healthy control group, the expression of GFAP proteins was found mainly at the level of the GCL layer. On the contrary, the diabetic mice treated with Placebo highlighted a significant increase in all retinal layers, showing the glial hyperactivation state due to the neurodegenerative inflammatory process. In fact, 100% of the diabetic mice of Placebo group showed a score in GFAP score≥23 (Table 2). The administration of Citicoline as well as of Nicotinamide produced a significant decrease in reactive gliosis, with a GFAP score≤3 in both cases. Such score surprisingly obtained a considerable improvement in the group treated with Cit.+Nic association, being equal to 1 in 94% of diabetic mice (≤2 in 100%).

TABLE 2

GFAP score evaluated for the several treatments.

| Score | Control | Placebo | Citicoline | Nicotinamide | Citicoline + Nicotinamide |
|---|---|---|---|---|---|
| 1 | 100% | 0% | 71% | 72% | 94% |
| 2 | | 0% | 22% | 18% | 6% |
| 3 | | 12.4% | 7% | 10% | 0% |
| 4 | | 32.8% | 0% | 0% | 0% |
| 5 | | 54.8% | 0% | 0% | 0% |

Figure 4:
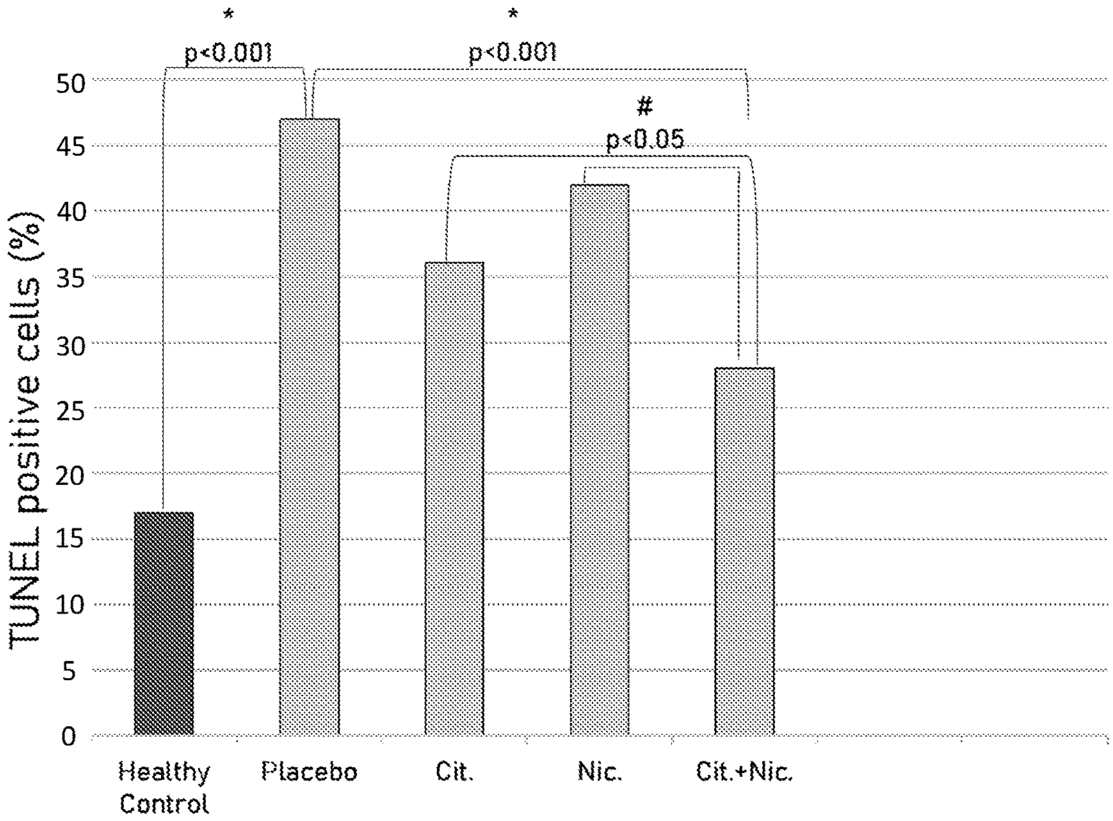
FIG. 4. Effect of the several treatments described in the Example 2 on the cell apoptosis (TUNEL assay).

(iv) Through TUNEL assay it was highlighted that the percentage of apoptotic cells in the GCL retinal layer was significantly higher in diabetic mice than non-diabetic control mice, thus showing an important increase in the apoptotic phenomena affecting the ganglion cells of retina after the neurodegenerative processes induced by diabetes (FIG. 4). Diabetic mice treated with citicoline only had a lower apoptosis rate with respect to the diabetic mice treated with the vehicle ($p<0.05$). Even the mice of Nic. group showed lower apoptosis levels than the diabetic mice treated with the vehicle but with not statistically significant levels. Surprisingly, the results of Cit+Nic group highlight a synergic effect in the reduction and prevention of apoptosis with a statistically significant difference with respect to the single treatments as well to the placebo group and without statistical significance with respect to the control group. Such result can be compared to the action synergy of the two active principles: multifactorial action mechanism of citicoline and anti-oxidant cellular action of nicotinamide. Such synergy is responsible for the strong protective effect on the cellular structures and for the prevention of apoptosis, thus guaranteeing an important neuroprotective effect.

Figure 5:
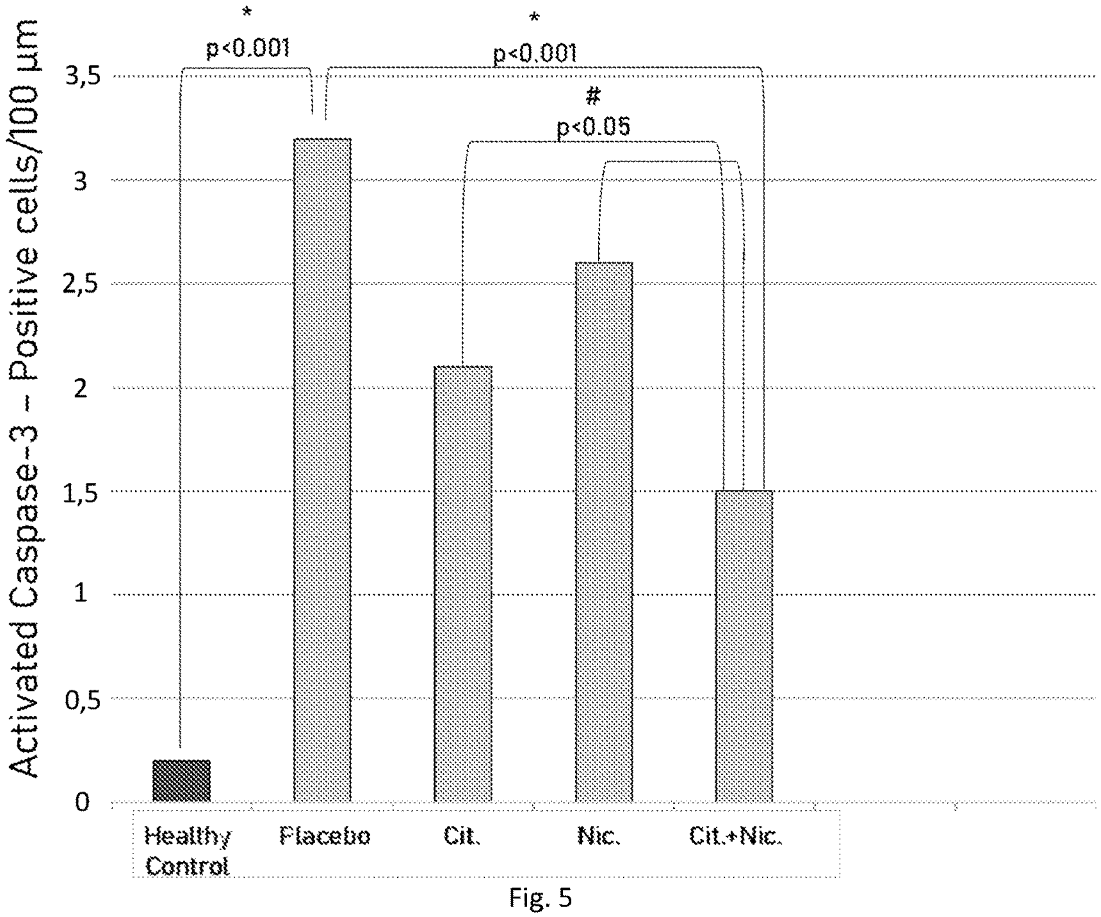
FIG. 5. Effect of the several treatments described in the Example 2 on the levels of Caspase-3.
Figure 6:
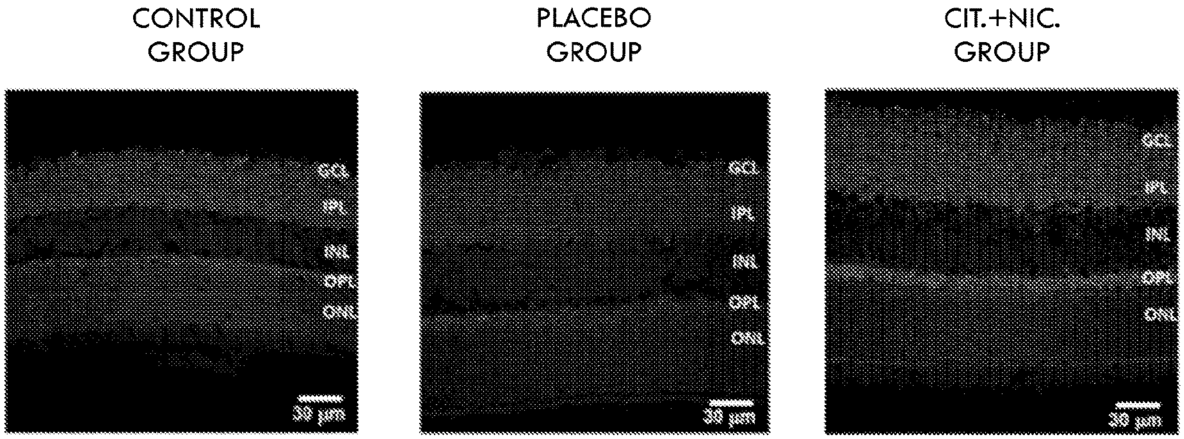
FIG. 6. Comparison of immunofluorescence of synaptophysin (red) between the healthy control group, the group treated with placebo and the group treated with Citicoline+ Nicotinamide.

(5) The anti-apoptotic and protection role of synapsis was confirmed by the results related to the levels of caspase-3 and synaptophysin found in the various groups. Caspase-3 is an enzyme involved in the cellular programmed death participating actively to the apoptotic process and the levels thereof result to be definitely increased during neurodegenerative processes. In db/db mice a statistically significant increase in the levels of caspase-3 with respect to the control group was highlighted. Such levels reduce considerably in Cit+Nic group with a statistically significant difference not only with respect to placebo group but even with respect to the single treatments administered alone (Cit.; Nic) (FIG. 5). Synaptophysin is a protein present in the pre-synaptic vesicles and represents a first index of synaptic loss and consequent neuronal death. In the db/db mice treated with Placebo we are witnessing a downregulation of synaptophysin, statistically significant with respect to the control group ($p<0.05$). In Cit group and in the Nic. one, we are witnessing a statistically significant increase in the levels of synaptophysin, which reaches the values of the healthy control in Cit+Nic group with a higher effectiveness with respect to the same singularly administered molecules (FIG. 6). Such result confirms again a powerful synergic effect of Citicoline+Nicotinamide association, in particular with its anti-apoptotic mechanism which would represent an important neuroprotective therapy for the neurodegenerative pathologies where the apoptosis represents the first movens of the neurodegenerative process.

Example 3. Clinical Observation on Patients Affected by Open-Angle Glaucoma

The neuroprotective effect of Citicoline+Nicotinamide association in oral solution according to the present invention was evaluated in a clinical observation performed on patients affected by open-angle glaucoma. The selected patients should have open-angle glaucoma diagnosis for at least 2 years, they should be controlled from the point of view of the intraocular pressure (IOP≤18 mmHg) with any hypotensive medical therapy, they should have a progression speed of the campimetric damage of at least 1 dB of mean defect (MD) lost per year (Rate of Progression—RoP), demonstrated through at least 4 visual fields in the 2 preceding years.

12 randomized patients were included in 4 groups:

CIT. GROUP—3 patients treated with citicoline in oral solution 10 ml/die corresponding to 500 mg/die of citicoline, in addition to the hypotensive therapy;

NIC. GROUP—3 patients treated with nicotinamide in oral solution 10 ml/die corresponding to 100 mg/die di nicotinamide, in addition to the hypotensive therapy;

CIT.+NIC. GROUP—3 patients treated with citicoline+ nicotinamide in oral solution 10 ml/die corresponding to 500 mg/die di citicoline and 100 mg/die of nicotinamide, in addition to the hypotensive therapy.

NT GROUP—3 patients treated with the hypotensive therapy only.

The patients were treated and followed for 6 months. At baseline and after 6 months of treatment complete eye examination including visual acuity, control of the intraocular pressure (IOP) with Goldmann tonometry (GAT); visual field testing, electro-functional and morphological examination were performed.

(1) The visual field testing was performed with automatic perimetry (HFA, Sita Standard 24-2 protocol; Zeiss, San Leandro, CA, USA). Such analysis represents the gold standard for diagnosis and follow-up of the glaucomatous patient and allows to represent graphically the extension in the space of the visual capability, by measuring even the peripheral vison thereof. Two analyses on each examination were performed and the second test was considered for the analysis. To perform the test, the patients were positioned in front of the instrument. After having rested forehead and chin inside the dome, with the covered unexamined eye, they started to fix a central target and pressed a button whenever they perceived against themselves aluminous stimulus, even if with poor intensity. MD was considered as perimetric index.

Then (2) electro-functional test was performed: electroretinogram from PERG pattern and of the PEV visual evoked potentials to evaluate the bioelectric responses respectively of the retinal ganglion cells and of the visual cortex evoked from the visual stimuli. The patients were positioned in an acoustically insulated semi-dark room, in front of the display surrounded by a uniform field of luminance of 5 cd/m2. The recordings at PERG and at PEV were performed by adopting the same visual stimuli: on 18×18-degree sized TV monitor a chessboard-like contrast modulation was shown, white and black elements alternating in a cadenced way in time (18 degrees of visual arc, contrast of 80% and a rate of two inversions per second). Such method allows to detect the maximum sensitivity and specificity of PERG and PEV in detecting retinal and post-retinal dysfunctions in glaucomatous eyes. The signal to PERG and PEV was recorded by a small electrode of Ag/AgCl positioned respectively above the lower eyelid and on the scalp. The transitory response to PERG is characterized by a number of waves with three subsequent peaks of negative, positive and negative polarity, respectively. In visually normal subjects, these peaks have the following latency time: 35.50 and 95 ms (N35, P50, N95—letter designates polarity, latency time number). The peak-peak widths were measured at PERG P50-N95 for each wave. The transitory response to PEV is characterized by a number of waves with three subsequent peaks of negative, positive, negative polarity respectively. In visually normal subjects, these peaks have these latency time 75, 100 and 145 ms (N75, P100, N145). The PEV P100 latency time for each one of the average waves displayed on the records was measured. During a recording session, simultaneous PERG and PEV were recorded at least twice (between two and six times) and the resulting waveforms were overlapped to verify the repeatability of results. During the recording session two subsequent waves having a difference in ms (for the latency time at PEV P100) and in μV (for the widths at PERG P50-N95 and PEV N75-P100) being lower than the intra-individual variability values (2 ms per pev P100 implied times and about ±0.18 μV for Widths PERG P50-N95 and PEV N75-P100) were considered superimposable, and then repeatable.

(3) The evaluation of the thickness of the layer of the RNFL nerve fibres was performed with spectral-domain optical coherence tomography SD-OCT (RTVue Model-RT100 version 3.5; Optovue Inc, Fremont, CA, USA). Such analysis allows a tomographic survey of retina capable of highlighting, through high-resolution cross sections, structural details of the cellular layers and of their plexuses and allows a qualitative and quantitative analysis of the retinal alterations. The patients were positioned in front of the instrument and invited to observe a luminous target: the instrument, once the ocular structure to be analysed is focused, performs the scanning. In OCT results, the average value of RNFL-T of four measurements per quadrant was considered: higher (RNFL-TS), lower (RNFL-TI), nasal (RNFL-TN) and temporal (RNFL-TT); the overall data obtained in all quadrants (average of 16 values) were identified as RNFL general (RNFL-TO).

At last, the patients were subjected to a questionnaire to evaluate adherence to therapy and possible adverse effects.

Only the data related to the worst eye were considered. For all tests, the significance level was fixed to $p<0.05$.

Results

In table 3 the features of the 12 patients at Baseline.

TABLE 3

| Features at baseline of patients | | | | |
|---|---|---|---|---|
| Parameters | Citicoline Group (3) | Nicotinamide Group (3) | Citicoline + Nicotinamide Group (3) | Not treated Group (3) |
| Average age | 63.9 | 63.1 | 62.9 | 64.8 |
| IOP | 14.3 (±2.2) | 13.8 (±2.5) | 14.1 (±2.3) | 14.5 (±2.4) |
| MD | −8.9 (±3.1) | −8.7 (±2.9) | −8.8 (±2.8) | −8.9 (±2.7) |
| PERG P50-N95 A (microV) | 1.21 (±0.24) | 1.16 (±0.43) | 1.09 (±0.33) | 1.23(±0.23) |
| PEV P100 IT (ms) | 127.2 (±7.51) | 128.5 (±7.24) | 126.3 (±6.78) | 126.9(±6.88) |
| RNFL-TO | 65.8 (±12.2) | 62 (±13.0) | 64.7 (±11.9) | 63.4(±12.1) |

In Table 4 the results after 6 months related to IOP, MD, PERG, PEV and the values related to the RNFL thickness.

TABLE 4

| Results in the various treatment groups after 6 months | | | | |
|---|---|---|---|---|
| After 6 months of treatment | Citicoline Group (3) | Nicotinamide Group (3) | Citicoline + Nicotinamide Group (3) | Not Treated Group (3) |
| IOP | 13.8 (±1.8) | 14.0 (±2.3) | 13.9 (±2.2) | 14.3 (±2.3) |
| MD | −8.70 (±2.8)* | −8.92 (±2.6)* | −8.10 (±2.5)* | −9.4 (±2.7) |
| PERG P50-N95 A (microV) | 1.77 (±0.27)* | 1.74 (±0.21)* | 2.29 (±0.21)*# | 1.10(±0.43) |
| PEV P100 IT (ms) | 119.1 (±7.22)* | 119.5 (±7.00) * | 114.3 (±6.89)*# | 127.3(±5.18) |
| RNFL-TO | 65.0 (±12.0)* | 61.1 (±12.5) * | 64.5 (±12.1)*# | 61.3(±11.8) |

*p < 0.05 with respect to the not treated group;
#p < 0.05 with respect to the other groups (citicoline; nicotinamide; not treated).

In the group treated with only Citicoline (Cit.) a significant improvement in MD with respect to the baseline was highlighted. Such improvement results to be statistically significant even with respect to the not treated group. In the group treated with Nicotinamide (Nic.) only, at the end of the study we are witnessing a lower reduction in the MD value with respect to the not treated group (NT). In the group treated with Cit.+Nic. association in oral solution we are surprisingly witnessing a marked improvement in MD. The comparison with the administrations of the various molecules tested individually brought to the light the synergic effect of the association by demonstrating a higher effectiveness of the same on the visual function.

The electro-functional evaluation highlighted an improvement in the parameters related to the width to PERG and to the latency time to PEV in all treated patients. In the not treated group we are witnessing a significant worsening of such parameters. A greater effectiveness with Cit+Nic association in oral solution is highlighted, with a statistically significant difference not only with respect to the not treated group but even with respect to the single treatments ($p<0.05$).

The morphological examination, at last, confirms the neuroprotective effectiveness on the retinal layers of the various treatments. In particular, Cit.+Nic. association results to be surprisingly the most effective one by stopping in a statistically significant way with respect to all groups the thickening of the nerve fibres. Even in this case the improvement obtained with the association results to be higher than the sum of the effect of the single molecules administered individually by confirming the action synergism of the two active principles. Such thickening results to be considerably marked in the not treated group. No adverse reactions for any treatment were recorded.

BIBLIOGRAPHY

1. Morreale Bubella R et al. Neuroprotection of patient with open-angle chronic Glaucoma: role of citicoline in oral solution". Ottica Fisiopatologica 2011.
2. Williams P A, et al. Vitamin B3 modulates mitochondrial vulnerability and prevents glaucoma in aged mice. Science 2017; 355, 756-760.

The invention claimed is:

1. A method of treating a subject having glaucoma comprising administering to the subject a therapeutically effective amount of an oral composition in the form of an aqueous solution comprising citicoline and nicotinamide.

2. The method according to claim 1, wherein the oral composition is administered once per day.

3. The method according to claim 1, wherein the citicoline is present in the oral composition in a concentration between 25 mg/ml and 100 mg/ml.

4. The method according to claim 1, wherein the nicotinamide is present in the oral composition in a concentration between 5 mg/ml and 20 mg/ml.

5. The method according to claim 1, wherein the ratio between citicoline and nicotinamide in the oral composition is between 2.5:0.5 and 10:2.

6. The method according to claim 1, wherein the oral composition further comprises potassium sorbate, sodium lactate, fructose, and/or citric acid.

7. The method according to claim 6, wherein in the oral composition the potassium sorbate is present in a concentration comprised between 1.34 mg/ml and 3.00 mg/ml, and/or wherein in the oral composition the sodium lactate is present in a concentration comprised between 2.5 mg/ml and 7 mg/ml, and/or wherein in the oral composition the fructose is present in a concentration comprised between 150 mg/ml and 400 mg/ml, and/or wherein in the oral composition the citric acid is present in a concentration comprised between 0.92 mg/ml and 2.00 mg/ml.

8. The method according to claim 1, wherein the oral composition further comprises one or more excipients and/or additives.

9. The method according to claim 1, wherein the bioavailability of citicoline and nicotinamide is comparable to that of intravenous administration.

10. The method according to claim 1, wherein the pH of the oral composition is between 3 and 5.

11. The method according to claim 1, wherein the density of the oral composition is between 1.116 and 1.156 g/ml.

* * * * *